US009316537B2

(12) United States Patent
Bamber et al.

(10) Patent No.: US 9,316,537 B2
(45) Date of Patent: Apr. 19, 2016

(54) SORTING MATERIALS USING A PATTERN RECOGNITION, SUCH AS UPGRADING NICKEL LATERITE ORES THROUGH ELECTROMAGNETIC SENSOR-BASED METHODS

(71) Applicant: MineSense Technologies Ltd., Vancouver (CA)

(72) Inventors: Andrew Sherliker Bamber, Vancouver (CA); Nicholas Barcza, London (GB); Andrew Csinger, Vancouver (CA)

(73) Assignee: MineSense Technologies Ltd., Vancouver (CA)

(*) Notice: Subject to any disclaimer, the term of this patent is extended or adjusted under 35 U.S.C. 154(b) by 0 days.

(21) Appl. No.: 13/830,453

(22) Filed: Mar. 14, 2013

(65) Prior Publication Data
US 2013/0201481 A1 Aug. 8, 2013

Related U.S. Application Data

(63) Continuation-in-part of application No. 13/358,931, filed on Jun. 29, 2012.

(60) Provisional application No. 61/640,749, filed on May 1, 2012, provisional application No. 61/502,772, filed on Jun. 29, 2011, provisional application No. 61/502,760, filed on Jun. 29, 2011.

(51) Int. Cl.
*G06F 7/00* (2006.01)
*G01J 3/00* (2006.01)
(Continued)

(52) U.S. Cl.
CPC . *G01J 3/00* (2013.01); *B07C 5/344* (2013.01); *G01N 23/12* (2013.01)

(58) Field of Classification Search
USPC .......................................... 700/223
See application file for complete search history.

(56) References Cited

U.S. PATENT DOCUMENTS 3,263,160 A 7/1966 Dolan et al.
3,337,328 A 8/1967 Lawyer
(Continued)

FOREIGN PATENT DOCUMENTS

CA 2629408 A1 11/2009
DE 3228447 C2 4/1986
(Continued)

OTHER PUBLICATIONS

Bamber, Andrew Sherliker, "Integrated Mining, Pre-Construction and Waste Disposal Systems for the Increased Sustainability of Hard Rock Metal Mining," Apr. 2008, pp. 29, 37-44, 85-89. <https://circle.ubc.ca/handle/2429/779>.

(Continued)

*Primary Examiner* — Kyle Logan
(74) *Attorney, Agent, or Firm* — Perkins Coie LLP

(57) ABSTRACT

A system and method of sorting mineral streams, for example laterite mineral ores, into appropriately classified valuable and waste streams for maximum recovery of value from the mineral stream, e.g., a stream of minerals includes receiving response data indicating reflected, absorbed or backscattered energy from a mineral sample exposed to a sensor, where the mineral sample is irradiated with electromagnetic energy. The system determines spectral characteristics of the mineral sample by performing spectral analysis on the response data of the mineral sample and identifies a composition of the mineral sample by comparing the spectral characteristics of the mineral sample to previously developed spectral characteristics of samples of known composition. The system then generates a sort decision for the mineral sample based on the comparison, where the sort decision is used in diverting the mineral sample to a desired destination e.g. pyrometallurgical treatment stages, or to a waste stream.

17 Claims, 5 Drawing Sheets

(51) Int. Cl.
  *B07C 5/344* (2006.01)
  *G01N 23/12* (2006.01)

(56) References Cited

U.S. PATENT DOCUMENTS

| | | | |
|---|---|---|---|
| 3,747,755 | A | 7/1973 | Senturia et al. |
| 4,030,026 | A | 6/1977 | Payne |
| 4,128,803 | A | 12/1978 | Payne |
| 4,241,835 | A | 12/1980 | Lockett |
| 4,300,097 | A | 11/1981 | Turner |
| 4,507,612 | A | 3/1985 | Payne |
| 4,659,989 | A | 4/1987 | Kerr |
| 5,236,092 | A | 8/1993 | Krotkov et al. |
| 5,523,690 | A | 6/1996 | Rowan |
| 6,078,018 | A | 6/2000 | Davis et al. |
| 6,664,914 | B2 | 12/2003 | Longstaff et al. |
| 7,161,672 | B2 | 1/2007 | Gornushkin et al. |
| 7,574,821 | B2 | 8/2009 | Furem |
| 7,595,489 | B2 | 9/2009 | Statham |
| 7,948,237 | B2 | 5/2011 | Kuzmin et al. |
| 7,965,167 | B2 | 6/2011 | Volker et al. |
| 8,100,581 | B2 | 1/2012 | Djordjevic |
| 8,446,156 | B2 | 5/2013 | Morrison |
| 8,515,008 | B2 | 8/2013 | Ullberg et al. |
| 8,664,595 | B2 | 3/2014 | Buhot et al. |
| 8,766,129 | B2 | 7/2014 | Kazakov et al. |
| 8,820,533 | B2 | 9/2014 | Shaw et al. |
| 8,855,809 | B2 | 10/2014 | Spencer et al. |
| 8,875,901 | B2 | 11/2014 | Wellwood et al. |
| 8,931,720 | B2 | 1/2015 | Box et al. |
| 8,937,282 | B2 | 1/2015 | Owen et al. |
| 8,957,340 | B2 | 2/2015 | Wellwood et al. |
| 8,958,905 | B2 | 2/2015 | Bamber et al. |
| 2006/0090379 | A1* | 5/2006 | Furem ............................ 37/443 |
| 2010/0091103 | A1 | 4/2010 | Peltonen et al. |
| 2011/0186660 | A1* | 8/2011 | Harding et al. .............. 241/24.1 |
| 2012/0148018 | A1 | 6/2012 | Sommer, Jr. |
| 2013/0026263 | A1 | 1/2013 | Bamber et al. |
| 2013/0073077 | A1* | 3/2013 | Wellwood et al. ............ 700/223 |
| 2013/0169961 | A1* | 7/2013 | Kraft ............................ 356/318 |
| 2013/0201481 | A1 | 8/2013 | Bamber et al. |
| 2013/0292307 | A1 | 11/2013 | Bamber et al. |
| 2013/0313169 | A1 | 11/2013 | Lapeyre et al. |
| 2014/0088876 | A1 | 3/2014 | Shiley et al. |
| 2014/0144342 | A1* | 5/2014 | Bye ............................... 102/311 |
| 2014/0225416 | A1 | 8/2014 | Harding et al. |
| 2014/0260801 | A1 | 9/2014 | Wellwood et al. |
| 2015/0108258 | A1 | 4/2015 | Bamber et al. |

FOREIGN PATENT DOCUMENTS

| | | | |
|---|---|---|---|
| WO | 2010028446 | A1 | 3/2010 |
| WO | 2011116417 | A1 | 9/2011 |
| WO | 2013016774 | A1 | 2/2013 |

OTHER PUBLICATIONS

International Search Report and Written Opinion for International Application No. PCT/CA2013/050330, Mailed Jul. 24, 2013, 9 pages.

N. G. Cutmore et al., "Ore Characterisation and Sorting," Minerals Engineering, vol. 10, No. 4., Jan. 1997, 6 pages.

Singh et al., "Application of image processing and radial basis neural network techniques for ore sorting and ore classification," Minerals Engineering, vol. 18, Jan. 2005, 9 pages.

International Search Report and Written Opinion for International Application No. PCT/CA2013/050336, mailing date Aug. 12, 2013, 12 pages.

International Search Report and Written Opinion for International Application No. PCT/IB2012/001560, Mail Date Nov. 29, 2012, 12 pages.

Kieba et al. "Differential Soil Impedance Obstacle Detection," U.S. Department of Energy Technical Report No. DE-FC26-02NT41318, Report Issue Date Jan. 17, 2005, 72 pages.

Yang et al., "Electromagnetic conductivities of rock cores: Theory and analog results," Geophysics, vol. 62, No. 6, Nov.-Dec. 1997, 15 pages.

International Search Report and Written Opinion for International Application No. PCT/CA2015/050683; mailed Oct. 21, 2015, 7 pages.

* cited by examiner

SORTING MATERIALS USING A PATTERN RECOGNITION, SUCH AS UPGRADING NICKEL LATERITE ORES THROUGH ELECTROMAGNETIC SENSOR-BASED METHODS

CROSS-REFERENCE TO RELATED APPLICATIONS

This application claims the benefit under 35 U.S.C. 119(e) of U.S. Provisional Application No. 61/640,749, filed on May 1, 2012, entitled "A Method For Upgrading Nickel Laterite Ores Through Electromagnetic Sensor-Based Methods," which is hereby incorporated by reference for all purposes in its entirety. This application is a continuation-in-part of U.S. application Ser. No. 13/538,931, filed Jun. 29, 2012, entitled "Extracting Mined Ore, Minerals or Other Materials Using Sensor-Based Sorting," which in turn claims the benefit of U.S. Provisional Application No. 61/502,772, filed on Jun. 29, 2011, entitled "Method for the Pre-Concentration of Mineral Ores" and U.S. Provisional Application No. 61/502,760, filed on Jun. 29, 2011, entitled "High Frequency Electromagnetic Spectrometer," all of which are hereby incorporated by reference for all purposes in their entireties.

BACKGROUND

Material extracted from the earth may be processed using various mining processes. Using various techniques, after materials are mined from the ground, they are typically blended to achieve as much as possible a homogeneous condition. Thereafter, those portions of the blended material that have no beneficial use or value are typically separated or extracted from the portions of the material that have beneficial use or value by various conventional means.

For example, rock material may be mined using explosives, excavated and then transported to crushers that crush the rock material into smaller grain size. After crushing, the rock material may be further ground finer in grinding mills. The process may also include a vibrating screen that classifies the crushed or ground material into desired grain sizes. Next, valuable minerals may be concentrated by removing unnecessary substances from the excavated rock material. The separation process may include leaching, flotation, gravity methods and magnetic separation, or concentration by pyrometallurgical methods.

After separating the most valuable fragments, metal may be extracted from the mineral. Common extraction methods include pyrometallurgy (a metal production method employing high temperatures), alternately hydrometallurgy (producing metal by leaching the raw material and precipitating the pure metal from the solution) and alternately electrometallurgy (a metal production method applying electricity).

BRIEF DESCRIPTION OF DRAWINGS

Embodiments of the present disclosure will be described and explained through the use of the accompanying drawings in which.

Figure 1:
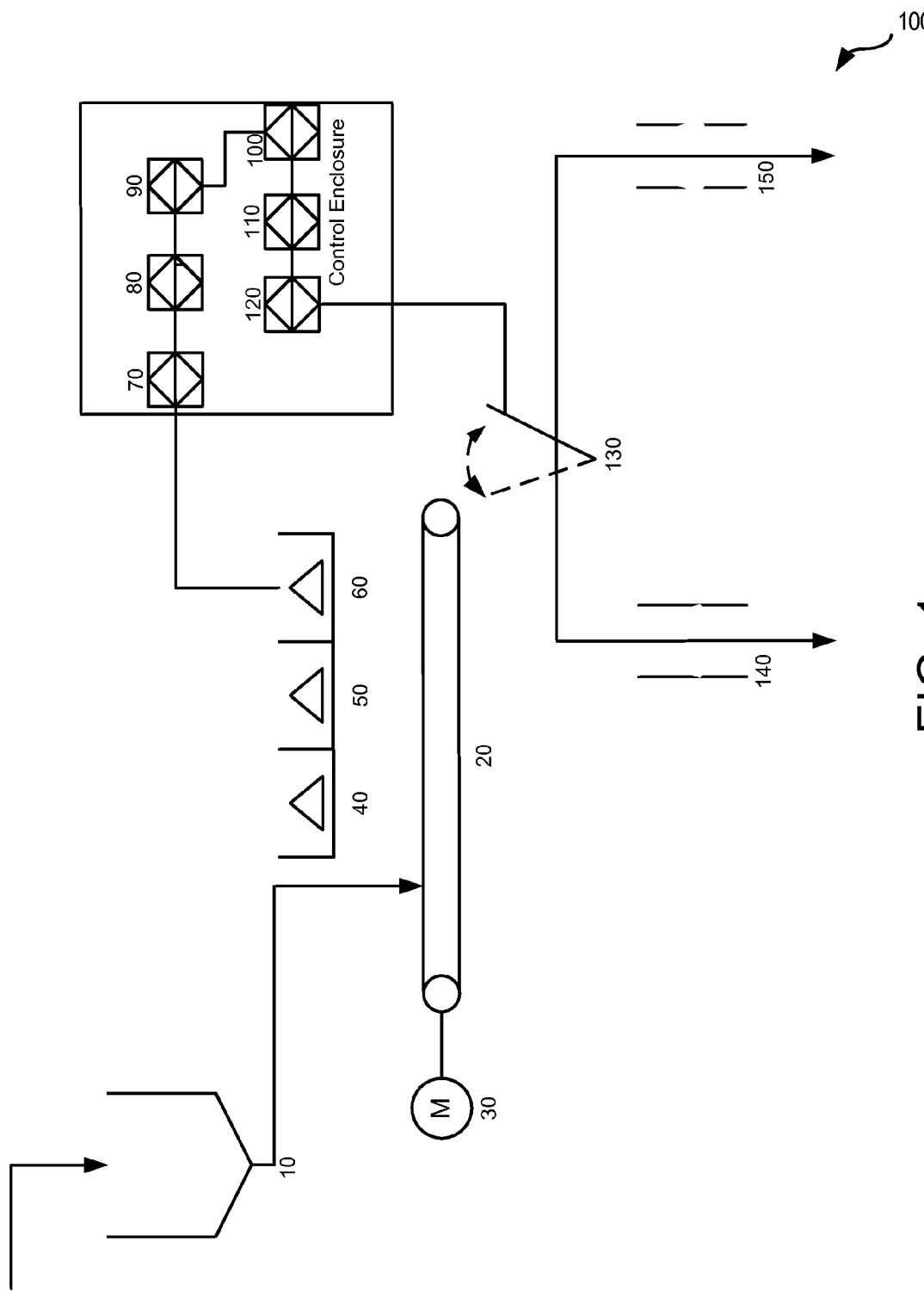
FIG. 1 illustrates an example of an arrangement for a sorting machine.

The drawings have not necessarily been drawn to scale. For example, the dimensions of some of the elements in the figures may be expanded or reduced to help improve the understanding of the embodiments of the present invention. Similarly, some components and/or operations may be separated into different blocks or combined into a single block for the purposes of discussion of some of the embodiments of the present invention. Moreover, while the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure.

DETAILED DESCRIPTION

In the field of mineral extraction and beneficiation, several methods exist for the extraction and beneficiation of lateritic nickel ores to ferronickel. Lateritic deposits are so named in cases where silica has been selectively leached from a nickel containing ultramafic magnesium-atuminosilicate deposit, selectively concentrating the nickel in heterogeneous proto-horizontal layers. Mining by mechanised open pit methods is common, however two principal beneficiation methods are used depending on the specific composition of the ore.

Iron-rich, predominantly limonitic ores are mined, blended, and treated hydrometallurgically, either by acid heap leach at atmospheric pressure, or by pressurized acid leach methods. Ferronickel is produced from the leachate by precipitation and electrorefining. Silica-rich predominantly saprolitic ores are treated pyrometallurgically firstly by calcining the crushed, mined and blended saprolite, and then smelting of the calcine, by either AC or DC methods. Lateritic deposits are seldom solely of one type or the other and generally contain significant quantities of both limonite and saprolite as well as intermediate or transition material, plus remnant silica basement material along with other diluents presented in a highly heterogeneous manner.

Each method is therefore compromised in the presence of too much of the other lithology (i.e., too much saprolite in the limonite when hydrometallurgical routes are selected, and too much limonite in the saprolite when pyrometallurgical methods are selected). Both treatment methods are compromised in the case of unilaterally low grades of nickel.

A novel solution to the common challenge of economic processing of laterites is described herein. It is possible to determine the variable chemical composition of unblended mineral samples or streams by exposing the mineral sample or stream to electromagnetic radiation and measuring a signal produced therefrom, such as an absorption, reflectance or Compton backscatter response. A machine comprising arrays of source-detector-type mineral sensors, coupled to high-speed, digital signal processing software incorporating rapid pattern recognition algorithms scans the ore stream in real-time and interprets the chemical composition of the ore. An array of physical diverters connected to the sensor array via a high-speed, real-time machine control layer are actuated to deflect the mineral sample or stream when the mineral composition as measured by the sensor array reaches a certain pre-determined value.

Embodiments of the present invention applied in the form of arrays of the described machines, sensibly arranged in a logical process sequence, can process large quantities of unblended laterite material mined unselectively at high throughput rates into streams of material simultaneously curated either for hydrometallurgical-optimal treatment, pyrometallurgical-optimal treatment, or as a waste product for disposal back into the mining void. Accordingly, in some embodiments, multiple economic streams from one deposit may simultaneously be produced using sensor-based methods.

Embodiments of the present invention described herein depart from conventional practice whereby in some described embodiments, the recovered value of mineral ores is maximized by preserving the natural heterogeneity of the mineral ore as much as possible by not blending the mineral ore prior to introducing it into a sorting system trained to recognise distinct species within the heterogeneous material. In some embodiments, a sorting system may then simultaneously classify the mineral ore into several fractions of arbitrary but variant value for processing in separate treatment streams (including a waste stream designated for disposal), thereby maximizing the recovered value of the mineral ore.

While multiple embodiments are disclosed, still other embodiments of the present disclosure will become apparent to those skilled in the art from the following detailed description, which shows and describes illustrative embodiments. As will be realized, embodiments of the present invention are capable of modifications in various aspects, all without departing from the scope of the present disclosure. Accordingly, the drawings and detailed description are to be regarded as illustrative in nature and not restrictive.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

FIG. 1 illustrates an example of an arrangement for a sorting machine. The sorting machine may include a feed mechanism, an electromagnetic source/detector array, and a control enclosure. The control enclosure may include an analog to digital signal conversion and signal analysis system, and a diverter array system connected to the control enclosure.

A sorter 100 may include a Teflon-lined, steep-sided feed bin suitable for accepting clay or rocky material feed 10, delivering material to a sorting conveyor 20 driven by variable speed motor 30. Material present on the sorting conveyor 20 may be detected by a scanning laser 40 which activates an electromagnetic energy source array 50. Consequent electromagnetic radiation absorption, reflectance or backscatter from the material present in the source energy field may be detected by a detector array 60. Analogue signals from the detector array may then be converted by analogue to digital signal converter 70 to digital form and be passed to a digital signal processing stage 80 where Fourier Analysis is performed to generate a discrete power spectrum analyzed by frequency or wavelength.

Discrete power spectrum data thus generated may then be compared using pattern recognition algorithms to determine the mineral content. Results of the pattern recognition algorithm may then be compared to pre-determined results in an embedded industrial computer 90. A diverter comprising relay/solenoid 110, actuator 120 and gate 130 may be controlled by the embedded industrial computer 90 via the programmable logic controller 100. Material with a recognized chemical composition above a certain pre-set value may be diverted to a product chute 140. Material with a recognized chemical composition below a certain pre-set value may be diverted to a waste chute 150.

Figure 2:
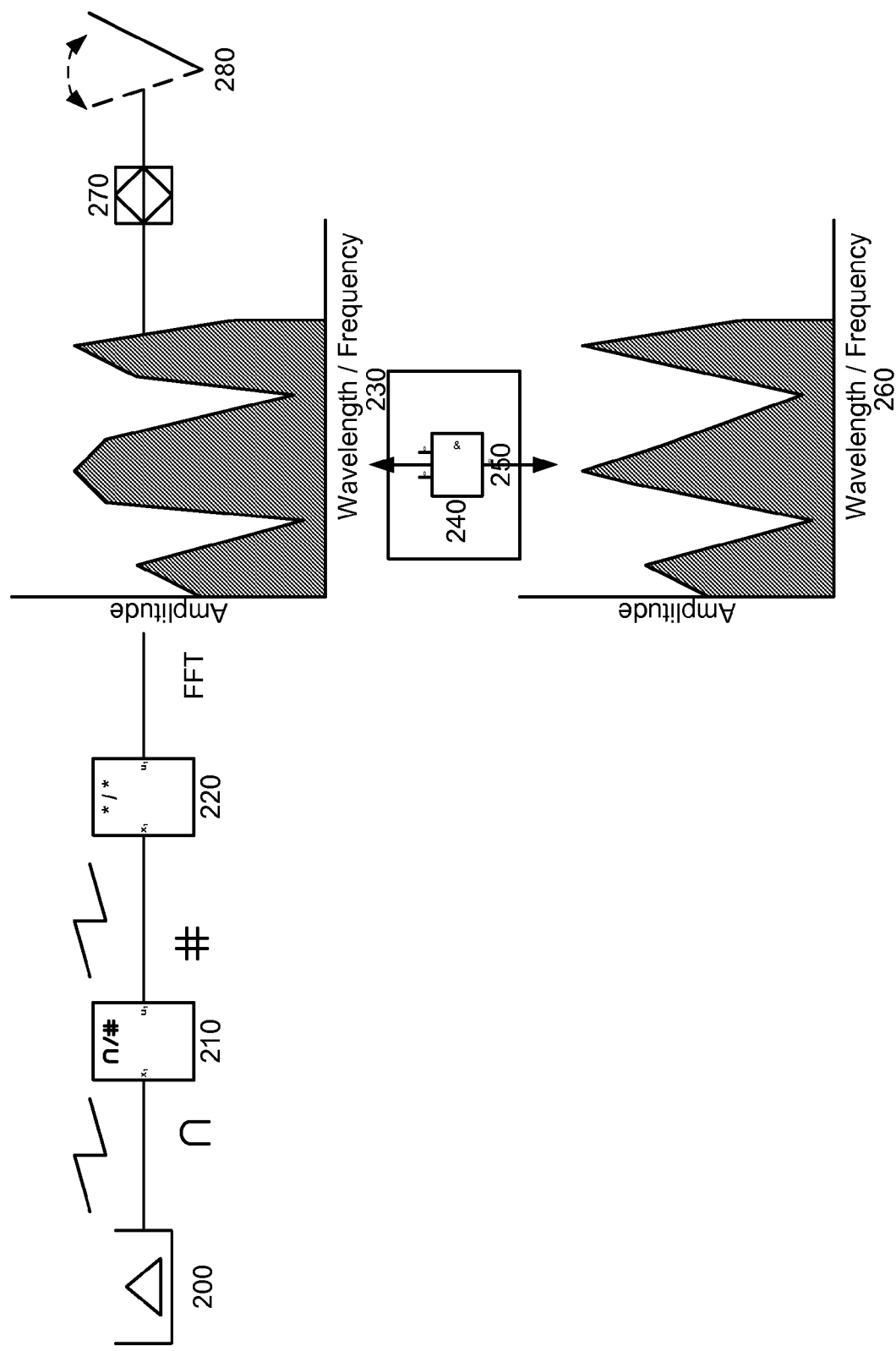
FIG. 2 illustrates an example of a control system with embedded pattern recognition and discrimination algorithms.

FIG. 2 illustrates an example of a control system with embedded pattern recognition and discrimination algorithms. The control system may include an analogue to digital conversion stage, a digital signal processing stage, a pattern recognition stage, comparator stage and a diverter array control stage.

Signals of arbitrary waveform, wavelength and frequency from a detector array 200 may be converted by analog to digital signal converter 210. Digital signals from the converter 210 may be passed to a Fourier Analysis stage where spectral data of amplitude/frequency or amplitude/wavelength format may be generated by Fast Fourier Transform implemented on a field programmable gate array (FPGA) 220 or other suitable device (e.g. a digital signal processor (DSP), application specific IC (ASIC), microcontroller, etc.). Arbitrary power spectra generated 230 in the Fourier Analysis stage 220 may be compared to previously determined and known spectra 260. Spectra of desired material may be recognized by pattern recognition algorithm 240 running on an embedded computer 250. Recognition of desired material may result in "accept" instructions being passed from the embedded computer 250 to the diverter array 280 via a programmable logic controller 270 or other suitable device (e.g. FPGA, DSP, ASIC, microcontroller, etc.). Recognition of undesired material may result in "reject" instructions being passed to a diverter array 280. The equivalency between like components in FIGS. 2 and 1 are evident—detector array 200 of FIG. 2 is equivalent to detector array 60 in FIG. 1; signal converter 210 to signal converter 70; embedded computer 250 to computer 90; diverter array 280 to diverter gate 130; PLC 270 to PLC 100 and so on.

Referring now to the pattern recognition algorithm in more detail, the concepts of recognition and identification as used in biometric security are introduced. Automated digital signal analysis is conventionally applied for pattern recognition using an exact matched, or identified, signal. In spectrum matching, both wavelength and amplitude, or frequency and amplitude of an arbitrary power spectrum are to be matched. Traditional pattern matching requires comparison of every inbound spectrum to the sample spectrum to achieve an exact match and is computationally very intensive and time consuming and therefore not practical in high-speed mineral recognition applications. Recognition is hereby differentiated from identification, or matching, for the purpose of the present system. As used in biometric security, for instance, recognition is the verification of a claim of identity, while identification is the determination of identity. These scenarios loosely correspond to the use of sensor telemetry for classification (e.g., sorting applications in the field) and characterization (e.g., analytical operations in the laboratory). To build further intuition, the biometric identification/recognition scenario will be further elucidated:

Identification

In the laboratory, a sample might be subjected to, for example, an X-ray Fluorescence sensor for analytic purposes. In the mining practice of interest, a spectral pattern is created in the lab using analytical procedures (i.e., samples from the deposit of interest are characterized or identified using analytical procedures in the lab). This is to say that the objective of the sampling is to yield the most accurate and precise result: a sensor-based assay. In this way the identity of a mineral sample as determined by sensor-based techniques is a priori determined. This template is programmed into field units so that results from new samples can be compared to it in quasi-real time.

The biometric analogy might go as follows: You are returning to your home country at one of its major international airports and have the option of using a kiosk equipped with an iris scanner. You simply approach the kiosk and present only your eye for examination by the scanner. The kiosk reads your iris and prints out a receipt with your name on it for you to present to a customs agent. The kiosk has clearly searched for a closest match to the sample you just provided, from a database of templates. You have been identified by the kiosk. Leaving aside the question of whether or not this is good security practice, it is clear that the kiosk is programmed to minimize the possibility of identity fraud (i.e., the incidence of false acceptance).

Recognition

In the field, samples are to be analyzed quickly—in quasi-real time—in order to produce economically viable results. There is neither time nor, as it turns out, need for exactitude in matching. A sample is to simply match the a priori pattern within a pre-determined tolerance; it is then recognized as a positive instance, or else it is classified as a negative instance.

It is therefore necessary only to recognize the emerging spectral pattern, based on the a priori identification described above, in time to make a classification decision.

The biometric analogy might go as follows: You are returning to your home country at one of its major international airports and have the option of using a kiosk equipped with an iris scanner. You approach the kiosk and present your passport, thereby making an identity claim. You then present your eye for examination by the scanner. The kiosk reads your iris and compares the sample to a stored template (derived, perhaps, from information encrypted in your passport). Identity has been rapidly confirmed by recognition of the subject based on a priori knowledge of the subject content. This is analogous to the pattern recognition algorithm deployed in various embodiments of the present invention.

The advanced pattern recognition methodology deployed involves pattern learning (or classification) of absorbed, reflected or backscattered energy from the irradiation of previously characterized mineral samples and pattern recognition comprising fuzzy analysis and resource-bounded matching of absorption, reflectance or backscattered spectra from newly irradiated mineral samples through a trained conditional random field (CRF) algorithm. The algorithms that match of absorption, reflectance or backscattered spectra may be resource-bounded, meaning that energy physics determines when measurement of a sample is complete.

Referring now to the CRF algorithm, CRF involves the "training" of the random field on known spectra, as well as the use of the random field under resource bounded conditions to rapidly recognize new spectra similar to the "trained" spectrum. In contrast to an ordinary matching algorithm which predicts a result for a single sample without regard to "neighboring" samples, the CRF algorithm deployed predicts a likely sequence of results for sequences of input samples analysed. Let X be an array observed spectral measurements with Y a corresponding array of random output spectra. Let $$S=[V,E] \quad (1)$$

be a set of spectra such that $$Y=(Yv)_{v \in V} \quad (2)$$

so that Y is indexed by the vertices of S. Then (X,Y) is a conditional random field when the random variables $Y_v$, conditioned on X, obey the Markov property $$p(Yv|X, Yw, w \neq v) = p(Tv|X, Yw, w \sim v) \quad (3)$$

where w~v means that w and v are neighbours or near neighbours in S. The conditional distribution $$p(Y|X) \quad (4)$$

is then modeled. Learning parameters θ are then obtained by maximum likelihood learning for $$p(Yi|Xi:\theta) \quad (5)$$

where all nodes have exponential family distributions and optimization is convex and can be solved by, e.g., gradient-descent algorithms. The learning, or characterization, phase involves identifying common characteristic spectra generated from a series of samples by repeated exposure of the spectral analyzer to the samples. These characteristic features may then be used for efficient and rapid spectrum recognition for new samples with similar spectra.

FIG. 2 references therefore a pattern recognition algorithm of the conditional random field type, using back-propagation when in the training mode to define matching coefficients e for the conditional random field, which additionally incorporates pseudo-random sampling, and boundary detection comprising confirmation of the spectral upper and lower bounds. The system is trained to recognize the presence of a range of typical mineral constituents in a matrix such as iron, aluminium, silica and magnesium present in a sample which is moving with reference to the sensor, calculate the specific and total concentration of each element in the sample and compare it to the pre-defined spectrum of known material obtained during the "training" phase of the algorithm development.

Other pattern recognition algorithms such as inter alia brute-force, nearest-neighbour, peak matching etc. may be used. As such, embodiments of the present invention are not limited to the particular algorithm described. For example, the peak frequencies from a few samples with certain amplitudes may be identified, and then each sample may be analyzed for peaks near those frequencies and above a certain amplitude.

Figure 3:
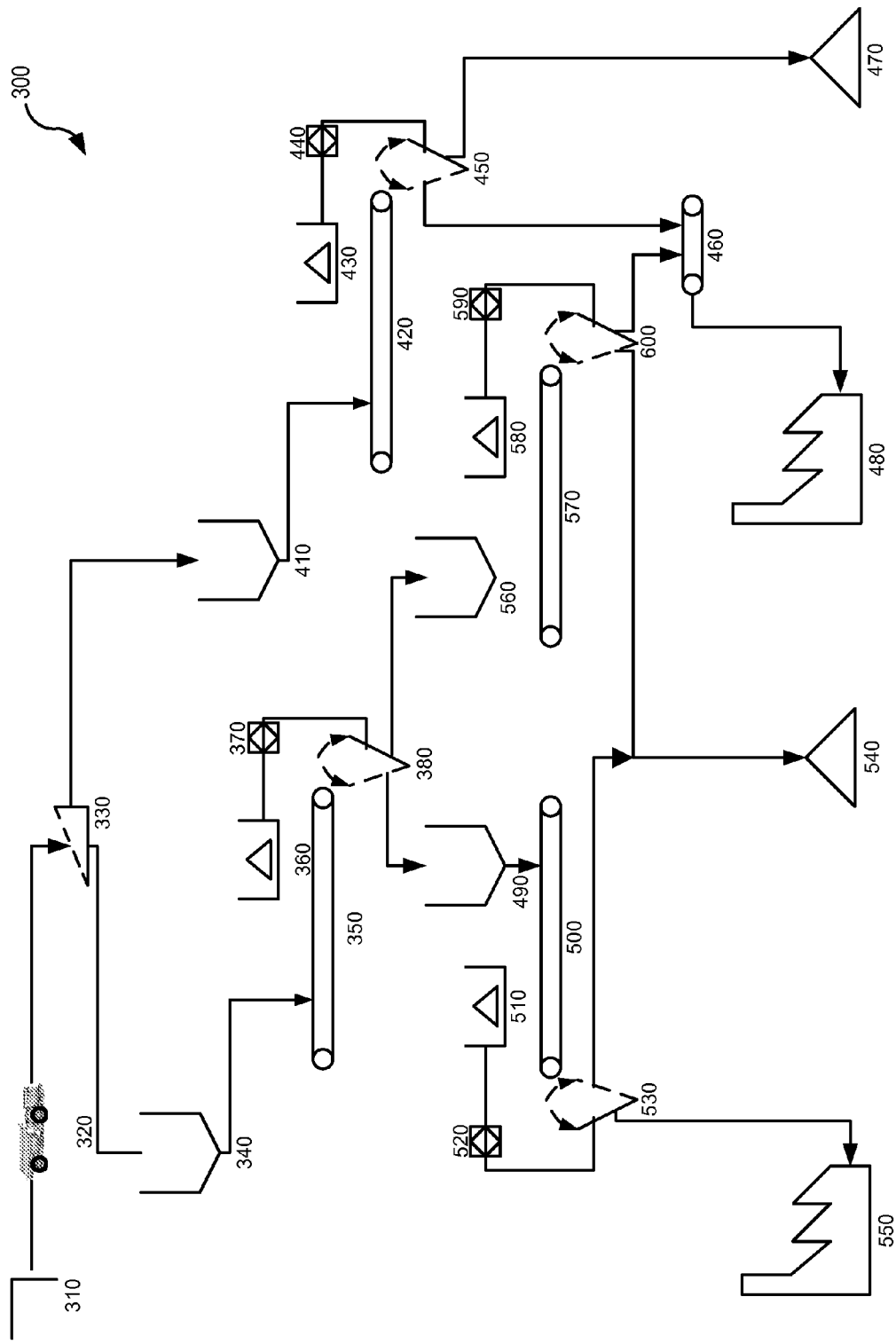
FIG. 3 illustrates an example of an arrangement of a sorting system.

FIG. 3 illustrates an example of an arrangement of a sorting system in an open pit mining application. Embodiments depicted in FIG. 3 may be used, for example to classify a pyrometallurgical process feed, a hydrometallurgical process feed and a waste product simultaneously from the same deposit. Typical bulk open pit mining equipment delivers unblended mineral feed to an ore sorting facility comprising arrays of electromagnetic sorting machines described. Saprolitic material produced by the sorting facility is delivered to pyrometallurgical plant 480. Limonitic material simultaneously recovered by the sorting facility is delivered to hydrometallurgical plant 550. Waste material simultaneously recovered by the sorting facility is delivered to waste piles 470, 540 for repatriation to the open pit.

Unblended laterite material 310 from the open pit may be delivered by truck 320 to coarse separator 330. Fine fractions from separator 330 underflow may be passed to fine sorter feed bin 340 where material may be held prior to delivery to sorting conveyor 350. Material travelling on the sorting conveyor 350 may be scanned by an array of electromagnetic sensors 360. Results from the electromagnetic sensors 360 may be passed to controller 370 which compares the sensor results to pre-set values and may instruct the diverter 380 to divert the material according to its chemical content. High iron limonitic material may be diverted to limonite sorter 490. High silica saprolitic material may be diverted to saprolite sorter feed bin 560.

High iron limonitic material from the sorting conveyor 350 may be passed to the limonite sorter feed bin 490 where material is held prior to delivery to sorting conveyor 500. Material traveling on the sorting conveyor 500 may be scanned by an array of electromagnetic sensors 510. Results from the electromagnetic sensors 510 may be passed to controller 520 which compares the sensor results to pre-set values and instructs diverter 530 to divert the material according to its chemical content. Material not suitable for treatment is diverted to the waste pile 540. Limonitic material suitable for treatment is passed via the limonite product conveyor to the hydrometallurgical facility 550.

Similarly high silica saprolitic material from the sorting conveyor 350 may be passed to saprolite sorter feed bin 560 where material may be held prior to delivery to sorting conveyor 570. Material travelling on the sorting conveyor may be scanned by an array of electromagnetic sensors 580. Results from the electromagnetic sensors 580 may be passed to the controller 590 which compares the sensor results to pre-set values and instructs the diverter 600 to divert the material according to its chemical content. Material not suitable for treatment is diverted to the waste pile 540. Saprolitic material suitable for treatment is passed via the saprolite product conveyor 460 to pyrometallurgical facility 480.

Coarse fractions from the separator 330 overflow may be passed to coarse sorter feed bin 410 where material may be held prior to delivery to the sorting conveyor. Material traveling on sorting conveyor 420 may scanned by an array of electromagnetic sensors 430. Results from the array of electromagnetic sensors 430 may be passed to controller 440 which compares the sensor results to pre-set values and instructs the diverter array 450 to divert the material according to its chemical content. High nickel saprolitic material may be diverted to saprolite product conveyor 460. Low nickel, high iron and high silica material may be diverted to the waste pile 470. Note that some elements may be combined together, such as a single controller that performs comparisons and instructs diverters.

Figure 4:
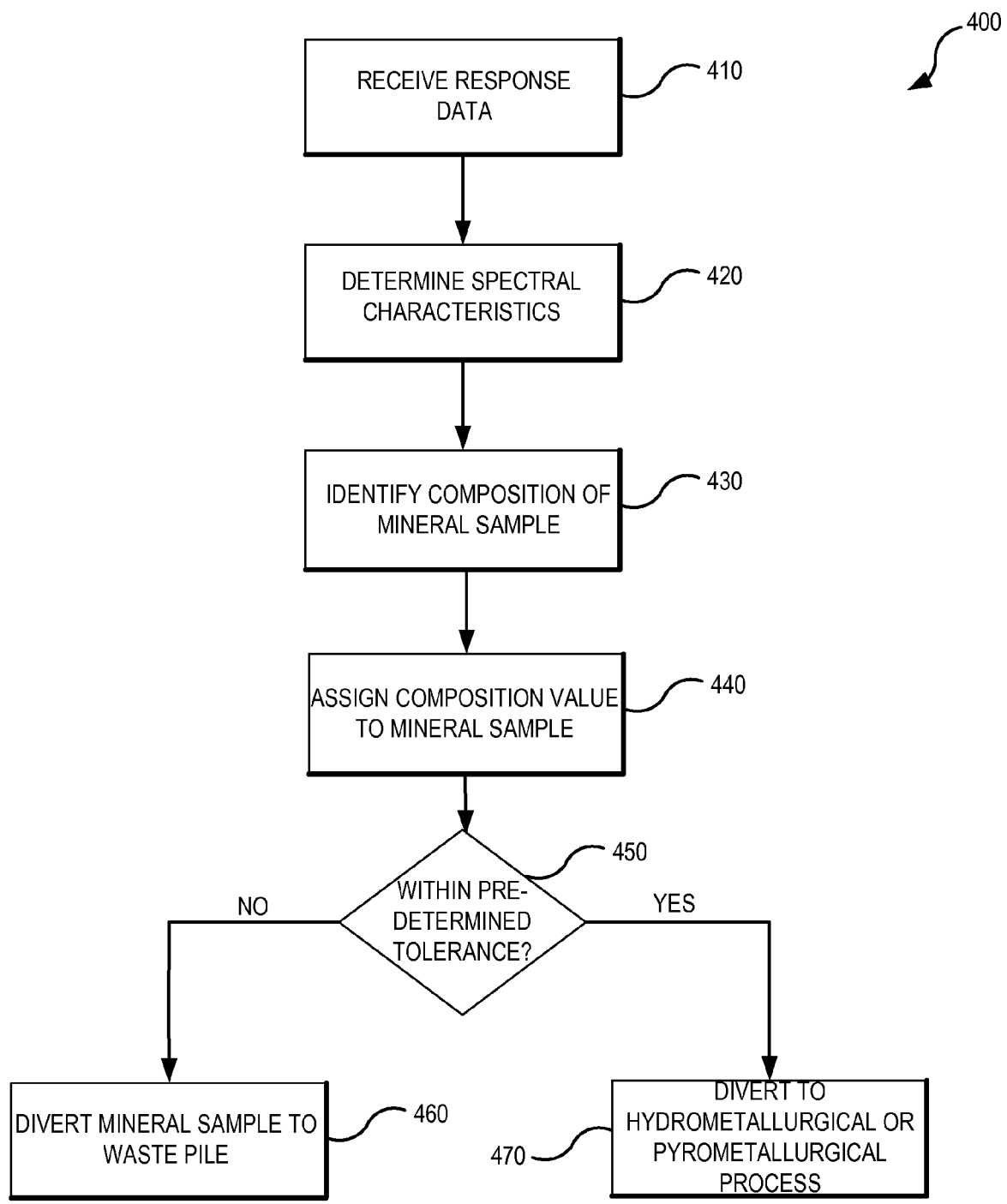
FIG. 4 is a flow chart having an example set of instructions for identifying mineral composition.

FIG. 4 is a flowchart having an example set of instructions for determining mineral content. The operations can be performed by various components such as processors, controllers, and/or other components. In receiving operation 410, response data from a mineral sample is received. The response data may be detected by a scanner that detects the response of the mineral sample to electromagnetic radiation (i.e., reflected or absorbed energy). An analog to digital converter may digitize the response data.

In determining operation 420, the spectral characteristics of the mineral sample may be determined. A spectral analysis may be performed on the response data to determine characteristics of the mineral sample. Characteristics may include frequency, wavelength, and/or amplitude. In some embodiments, characteristics include other user-defined characteristics.

In identifying operation 430, a composition of the mineral sample is identified by comparing the characteristics of the mineral sample to characteristics of known mineral samples. Pattern matching algorithms may be used in identifying the composition.

In assigning operation 440, a composition value is assigned to the mineral sample.

In decision operation 450, it is determined whether the composition value is within a predetermined tolerance of composition values. In reject operation 460, the assigned value of the composition is not within the predetermined tolerance (i.e., the characteristics do not fit with in a pattern), and, thus, the mineral sample is diverted to a waste pile. In accept operation 470, the assigned value of the composition is within the predetermined tolerance (i.e., the characteristics fit within a pattern), and thus, the mineral sample is diverted to a hydrometallurgical or pyrometallurgical process.

Computer System Overview

Figure 5:
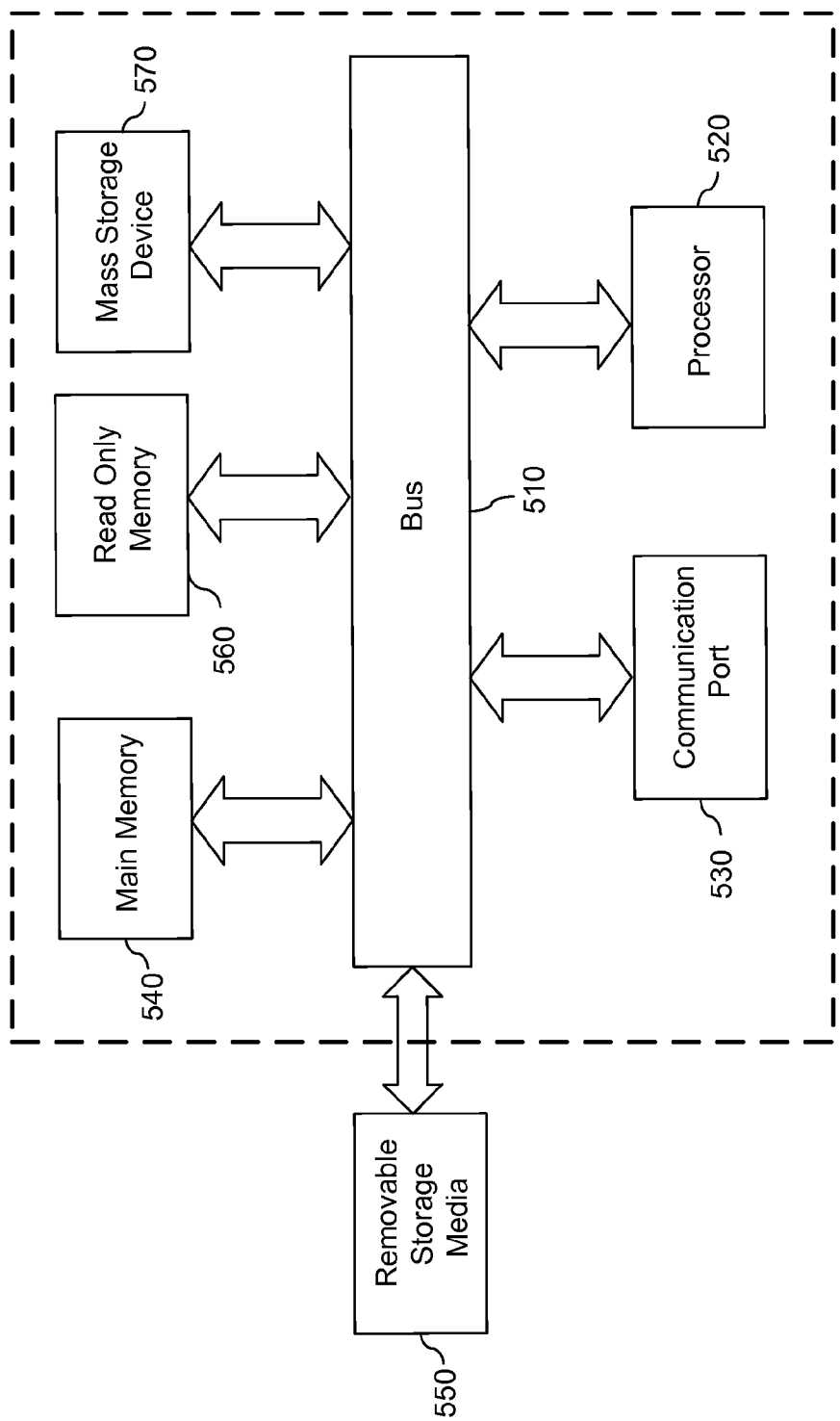
FIG. 5 an example of a computer system with which one or more embodiments of the present disclosure may be utilized.

Embodiments of the present invention include various steps and operations, which have been described above. A variety of these steps and operations may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 5 is an example of a computer system 500 with which embodiments of the present invention may be utilized. According to the present example, the computer system includes a bus 510, at least one processor 520, at least one communication port 530, a main memory 540, a removable storage media 550, a read only memory 560, and a mass storage 570.

Processor(s) 520 can be any known processor, such as, but not limited to, an Intel® Itanium® or Itanium 2® processor(s); AMD® Opteron® or Athlon MP® processor(s); or Motorola® lines of processors. Communication port(s) 530 can be any of an RS-232 port for use with a modem-based dialup connection, a 10/100 Ethernet port, or a Gigabit port using copper or fiber. Communications may also take place over wireless interfaces. Communication port(s) 530 may be chosen depending on a network such as a Local Area Network (LAN), Wide Area Network (WAN), or any network to which the computer system 500 connects.

Main memory 540 can be Random Access Memory (RAM) or any other dynamic storage device(s) commonly known in the art. Read only memory 560 can be any static storage device(s) such as Programmable Read Only Memory (PROM) chips for storing static information such as instructions for processor 520.

Mass storage 570 can be used to store information and instructions. For example, hard disks such as the Adaptec® family of SCSI drives, an optical disc, an array of disks such as RAID, such as the Adaptec family of RAID drives, or any other mass storage devices may be used.

Bus 510 communicatively couples processor(s) 520 with the other memory, storage and communication blocks. Bus 510 can be a PCI/PCI-X or SCSI based system bus depending on the storage devices used.

Removable storage media 550 can be any kind of external hard-drives, floppy drives, IOMEGA® Zip Drives, Compact Disc-Read Only Memory (CD-ROM), Compact Disc-Re-Writable (CD-RW), and/or Digital Video Disk-Read Only Memory (DVD-ROM).

Although not required, aspects of the invention may be practiced in the general context of computer-executable instructions, such as routines executed by a general-purpose data processing device, e.g., a server computer, wireless device or personal computer. Those skilled in the relevant art will appreciate that aspects of the invention can be practiced with other communications, data processing, or computer system configurations, including: Internet appliances, hand-held devices (including personal digital assistants (PDAs)), wearable computers, all manner of cellular or mobile phones (including Voice over IP (VoIP) phones), dumb terminals, multi-processor systems, microprocessor-based or programmable consumer electronics, set-top boxes, network PCs, mini-computers, mainframe computers, and the like.

Aspects of the invention can be embodied in a special purpose computer or data processor that is specifically programmed, configured, or constructed to perform one or more of the computer-executable instructions explained in detail herein. While aspects of the invention, such as certain functions, are described as being performed exclusively on a single device, the invention can also be practiced in distributed environments where functions or modules are shared among disparate processing devices, which are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the invention may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme).

CONCLUSION

As one of ordinary skill in the art will appreciate based on the detailed description provided herein, and various novel concepts are realized, some of which are listed below:

1. A source-detector type electromagnetic sorting system comprising:
   a. a device for the introduction of mineral feed to the sensor;
   b. a device for the generation of a range of excitation beams;
   c. a scanner for the detection of resulting reflected, absorbed, or backscattered energy;
   d. an analog to digital converter to digitize both the signal in (c);
   e. a software program for signal analysis, data recording, and process control;
   f. a control system for processing signal outputs; and
   g. a diverter connected to the control system for the diversion of minerals.
2. The source-detector type electromagnetic sorting system of claim 1, wherein the software program comprises:
   a. a subroutine to convert incoming analog signals to digital format
   b. a subroutine to express spectral content of the converted analog signal
   c. a subroutine to perform spectral analysis on both digitized signals in 1(c), determining frequency or wavelength content and amplitude;
   d. a subroutine to calibrate the system;
   e. a subroutine to record the response data in (b) and (c) along with additional user defined fields;
   f. a subroutine to compare spectral response data to previously recorded spectral data from samples of known composition by means of conditional random field analysis;
   g. a subroutine to generate a sort signal based on the comparison in (f); and
   h. a graphical user interface to control operation and data recording.
3. A method of determining the spectral response of a mineral sample under irradiation by electromagnetic means using said system comprising:
   a. providing said source detector sensing and sorting system;
   b. exposing said sensor to a mineral sample;
   c. converting the spectral response of said mineral sample to digital format by means of the software program in 1(e);
   d. measuring the spectral response of said mineral sample to said sensor by means of the software program in 1(e); and
   e. converting the measured response (c) into a power spectrum by means of the software program described in 1(e).
   f. assigning an appropriate threshold of acceptance for spectral responses above a certain pre-determined value and 'training' the algorithm to recognize those responses
4. A method of determining the mineral composition of an unknown sample using said sensor comprising:
   a. providing said system;
   b. measuring the spectral response due to the unknown sample;
   c. using the software program described in 1(e) to compare the measured data in (b) to previously recorded response data from samples of known grade as describe in 3; and
   d. using said software program to assign a compositional value to the unknown sample based on the comparison in (c).
5. A method of discriminating mineral samples based on spectral response using said sensor comprising:
   a. providing said system;
   b. determining characteristic spectral response of the mineral sample as described in 3 and 4;
   c. using the software program in 1(e) to compare the values determined in (b) to predefined spectra of previously characterized mineral samples by means of the conditional random field algorithm described; and
   d. using the control system described in 1(f) to control the diverter system based upon results of the comparison described in (c).
6. A method of automatically rejecting or accepting mineral samples based on spectral response using the system of claim 1 comprising the steps of:
   a. providing said system;
   b. discriminating between sample materials;
   c. using the software program in 1(e) to generate a sort decision based on the discrimination in (b); and
   d. effecting the sort based on the decision in (c) by means of the sorting mechanism described in 1 and 2.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain embodiments of the invention are presented below in certain claim forms, but the applicant contemplates the various aspects of the invention in any number of claim forms. For example, while only one aspect of the invention is recited as a means-plus-function claim under 35 U.S.C. sec. 112, sixth paragraph, other aspects may likewise be embodied as a means-plus-function claim, or in other forms, such as being embodied in a computer-readable medium. (Any claims intended to be treated under 35 U.S.C. §112, ¶6 will begin with the words "means for", but use of the term "for" in any other context is not intended to invoke treatment under 35 U.S.C. §112, ¶6.) Accordingly, the applicant reserves the right to pursue additional claims after filing this application to pursue such additional claim forms, in either this application or in a continuing application.

As one of ordinary skill in the art will appreciate based on the detailed description provided herein, and various novel concepts are realized. The Abstract of the Disclosure is provided to comply with 37 C.F.R. section 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment.

We claim:

1. A method of sorting a stream of minerals, comprising:
   irradiating a mineral sample with electromagnetic energy to thereby generate reflected, absorbed, or backscattered energy from the mineral sample;
   measuring the reflected, absorbed or backscattered energy generated by irradiating the mineral sample with a sensor configured to measure reflected, absorbed or backscattered energy;
   determining spectral characteristics of the mineral sample by performing spectral analysis on the measured reflected, absorbed or backscattered energy generated by irradiating the mineral sample,
      wherein the spectral characteristics include at least one of frequency content, wavelength content, or amplitude of the response data;
   identifying a composition of the mineral sample by comparing the spectral characteristics of the mineral sample to previously developed spectral characteristics of samples of known composition,
      wherein the spectral characteristics of samples of known composition are developed using at least one of: conditional random field algorithms, Bayesian network, one or more Markov models, neural networks, or fuzzy logic techniques; and
   generating a sort decision for the mineral sample based on the comparison,
      wherein the sort decision is used in diverting the mineral sample to a desired destination.

2. The method of claim 1 further comprising collecting spectral response data from a series of mineral samples irradiated with electromagnetic energy and exposed to a sensor to develop the spectral characteristics of samples of known composition.

3. The method of claim 1 wherein comparing the spectral characteristics of the mineral sample to previously developed spectral characteristics of samples of known composition includes matching the spectral characteristics of the mineral sample to previously developed pattern sets.

4. The method of claim 1 wherein identifying a composition of the mineral sample includes assigning a compositional value to the mineral sample based on the comparison.

5. The method of claim 4 wherein the mineral sample is diverted to an accept pile when the compositional value is within a predetermined variation of the previously developed spectral characteristics.

6. At least one tangible computer-readable medium carrying instructions, which when executed by at least one processor, determines a composition of a mineral sample, comprising:
measuring reflected, absorbed or backscattered energy generated by exposing an unblended mineral sample to electromagnetic radiation;
comparing the measured reflected, absorbed or backscattered energy to previously recorded response data from samples of known composition to identify a composition of the unblended mineral sample; and
assigning a compositional value to the unblended mineral sample based on the comparison.

7. The at least one tangible computer-readable medium of claim 6, wherein the unblended mineral sample is a laterite, and wherein the sort signal is used to divert the mineral sample to one of: a hydrometallurgical process, a pyrometallurgical process, or a waste pile.

8. The at least one tangible computer-readable medium of claim 6, wherein the instructions, which when executed by the at least one processor, further comprise:
transporting the unblended mineral sample into a source field.

9. The at least one tangible computer-readable medium of claim 6, wherein the instructions, which when executed by the at least one processor, further comprise:
generating a signal based on the compositional value.

10. The at least one tangible computer-readable medium of claim 9, wherein the signal is a sort signal used to divert the unblended mineral sample to a desired location.

11. A system for sorting minerals, comprising:
a device to introduce unblended mineral samples to a sensor;
a device to generate electromagnetic energy to apply to the unblended mineral samples and thereby generate reflected, absorbed or backscattered energy from the unblended mineral sample;
a scanner configured to measure the reflected, absorbed or backscattered energy generated by applying electromagnetic energy to the unblended mineral samples;
a means for comparing the reflected, absorbed or backscattered energy to previously determined response data of samples of known composition to determine a composition of the unblended mineral samples.

12. The system of claim 11 further comprising:
an analog to digital converter to digitize the measured reflected, absorbed or backscattered energy;
a control system to process signal outputs; and
a diverter coupled to the control system for the diversion of the mineral samples.

13. The system of claim 11 further comprising a graphical user interface to control operation and record data.

14. The system of claim 11 wherein the response data of samples of known composition includes spectral characteristics.

15. The system of claim 14 wherein the spectral characteristics of samples of known composition are developed using at least one of: conditional random field algorithms, Bayesian network, one or more Markov models, neural networks, or fuzzy logic techniques.

16. A method of maximizing the recovered value of mineral ores, comprising:
extracting unblended mineral ore from a mine bench or pit using a mechanical excavator or similar earthmoving device;
delivering the unblended mineral ore to a haul truck or conveyor belt using the excavator;
transporting the unblended mineral ore to a first mineral sorting system, the first mineral sorting system configured to:
apply electromagnetic radiation to the unblended mineral ore,
detect a response of the mineral ore to the electromagnetic radiation, and
compare the response data to previously determined response data of samples of known composition to determine the composition of the unblended mineral ore;
classifying the unblended mineral ore, based on the comparison, into a first mineral product and a second mineral product;
transporting the first mineral product to a second mineral sorting system, the second mineral sorting system configured to:
apply electromagnetic radiation to the first mineral product;
detect a response of the first mineral product to the electromagnetic radiation, and
compare the response data to previously determined response data of samples of known composition to determine the composition of the first mineral product;
classifying the first mineral product, based on the comparison, into a final first mineral product and waste product;
transporting the second mineral product to a third mineral sorting system, the third mineral sorting system configured to:
apply electromagnetic radiation to the second mineral product;
detect a response of the second mineral product to the electromagnetic radiation, and
compare the response data to previously determined response data of samples of known composition to determine the composition of the second mineral product;
classifying the second mineral product, based on the comparison, into a final second mineral product and waste product.

17. The method of claim 16, wherein:
the final first mineral product is conditioned for pyrometallurgical treatment,
the final second mineral product is conditioned for hydrometallurgical treatment, and
the waste product is conditioned for disposal as a waste product.

* * * * *